US010869621B2

(12) United States Patent
Yamashita et al.

(10) Patent No.: US 10,869,621 B2
(45) Date of Patent: Dec. 22, 2020

(54) BIOLOGICAL INFORMATION MEASUREMENT DEVICE AND METHOD FOR DETERMINING CORRECTNESS OF BIOLOGICAL INFORMATION

(71) Applicants: OMRON HEALTHCARE CO., LTD., Kyoto (JP); OMRON Corporation, Kyoto (JP)

(72) Inventors: Shingo Yamashita, Muko (JP); Naoki Maeda, Kyoto (JP)

(73) Assignees: OMRON HEALTHCARE CO., LTD., Kyoto (JP); OMRON CORPORATION, Kyoto (JP)

(*) Notice: Subject to any disclaimer, the term of this patent is extended or adjusted under 35 U.S.C. 154(b) by 59 days.

(21) Appl. No.: 16/203,746

(22) Filed: Nov. 29, 2018

(65) Prior Publication Data

US 2019/0090787 A1   Mar. 28, 2019

Related U.S. Application Data

(63) Continuation of application No. PCT/JP2017/020127, filed on May 30, 2017.

(30) Foreign Application Priority Data

Jun. 1, 2016  (JP) .................................. 2016-110369

(51) Int. Cl.
*A61B 5/11* (2006.01)
*A61B 5/1171* (2016.01)
(Continued)

(52) U.S. Cl.
CPC .......... *A61B 5/1176* (2013.01); *A61B 5/0002* (2013.01); *A61B 5/024* (2013.01);
(Continued)

(58) Field of Classification Search
None
See application file for complete search history.

(56) References Cited

U.S. PATENT DOCUMENTS 8,679,012 B1  3/2014  Kayyali
2002/0013717 A1* 1/2002  Ando .................. A61B 5/22
                                                    705/4
(Continued)

FOREIGN PATENT DOCUMENTS

CN        1451354     10/2003
CN       101176654    5/2008
(Continued)

OTHER PUBLICATIONS

International Search Report dated Aug. 1, 2017 in International Application No. PCT/JP2017/020127.
(Continued)

*Primary Examiner* — Fayyaz Alam
(74) *Attorney, Agent, or Firm* — Wenderoth, Lind & Ponack, L.L.P.

(57) ABSTRACT

A biological information measurement device includes: an information input request unit configured to request an input of identification information at each of a plurality of timings after measurement of the biological information is started; a personal identification unit configured to determine whether a user wearing the biological information measurement device is a pre-registered person in synchronization with each of the plurality of timings, based on the identification information; an identification result information generation unit configured to generate identification result information indicative of a relationship between a first number of times that the request is made by the information input request unit and a second number of times that the user is determined to be the pre-registered person by the personal identification unit; and a correctness determination unit configured to
(Continued)

determine correctness of the biological information on the basis of the identification result information.

13 Claims, 8 Drawing Sheets

(51) Int. Cl.

| | | |
|---|---|---|
| *G06K 9/00* | (2006.01) | |
| *A61B 5/00* | (2006.01) | |
| *A61B 5/117* | (2016.01) | |
| *A61B 5/0205* | (2006.01) | |
| *G16H 50/30* | (2018.01) | |
| *G16H 40/63* | (2018.01) | |
| *G16H 10/60* | (2018.01) | |
| *A61B 5/024* | (2006.01) | |
| *A61B 5/1172* | (2016.01) | |
| *G16H 10/20* | (2018.01) | |
| *A61B 5/0402* | (2006.01) | |
| *G06F 21/32* | (2013.01) | |
| *G06K 9/03* | (2006.01) | |
| *G06Q 40/08* | (2012.01) | |

(52) U.S. Cl.
CPC ............ *A61B 5/0205* (2013.01); *A61B 5/117* (2013.01); *A61B 5/1118* (2013.01); *A61B 5/1172* (2013.01); *A61B 5/4809* (2013.01); *A61B 5/681* (2013.01); *A61B 5/6824* (2013.01); *G06K 9/00342* (2013.01); *G16H 10/60* (2018.01); *G16H 40/63* (2018.01); *G16H 50/30* (2018.01); *A61B 5/0402* (2013.01); *A61B 2562/043* (2013.01); *G06F 21/32* (2013.01); *G06K 9/00087* (2013.01); *G06K 9/036* (2013.01); *G06K 2009/00932* (2013.01); *G06K 2009/00939* (2013.01); *G06Q 40/08* (2013.01); *G16H 10/20* (2018.01)

(56) References Cited

U.S. PATENT DOCUMENTS

| | | |
|---|---|---|
| 2003/0190062 A1 | 10/2003 | Noro et al. |
| 2005/0049501 A1 | 3/2005 | Conero et al. |
| 2008/0112627 A1 | 5/2008 | Oda |
| 2008/0252412 A1 | 10/2008 | Larsson et al. |
| 2012/0086550 A1 | 4/2012 | LeBlanc et al. |
| 2013/0050221 A1 | 2/2013 | Yamaguchi |
| 2015/0118658 A1* | 4/2015 | Mayou ............... A61B 5/746 434/127 |
| 2020/0126660 A1* | 4/2020 | Costantino ............ G16H 70/40 |

FOREIGN PATENT DOCUMENTS

| | | |
|---|---|---|
| CN | 102844782 | 12/2012 |
| JP | 2001-318892 | 11/2001 |
| JP | 2002-055956 | 2/2002 |
| JP | 2002-238877 | 8/2002 |
| JP | 2007-35050 | 2/2007 |
| JP | 2007-193447 | 8/2007 |
| JP | 2008-228924 | 10/2008 |
| JP | 2011-200412 | 10/2011 |
| JP | 2012-010955 | 1/2012 |
| JP | 2013-109736 | 6/2013 |
| JP | 2013-212315 | 10/2013 |

OTHER PUBLICATIONS

International Preliminary Report on Patentability and Written Opinion of the International Searching Authority dated Jul. 14, 2017 in International Application No. PCT/JP2017/020127.
Extended European Search Report dated Sep. 23, 2019 in corresponding European Patent Application No. 17806687.4.
Notice of Reasons for Refusal dated Jun. 23, 2020 in corresponding Japanese Paten Application No. 2016-110369, with Machine translation.
Chinese Office Action dated Oct. 10, 2020 in corresponding Chinese Patent Application No. 201780032738.8 with English translation.

* cited by examiner

BIOLOGICAL INFORMATION MEASUREMENT DEVICE AND METHOD FOR DETERMINING CORRECTNESS OF BIOLOGICAL INFORMATION

CROSS-REFERENCE TO RELATED APPLICATION(S)

This application is a continuation of PCT application No. PCT/JP2017/020127, which was filed on May 30, 2017 based on Japanese Patent Application No. 2016-110369 filed on Jun. 1, 2016, the contents of which are incorporated herein by reference.

BACKGROUND

1. Technical Field

The present invention relates to a biological information measurement device and a method for determining correctness of biological information.

2. Background Art

As a personal authentication technology for enabling only a specific person to use a device, a service or the like, a technology of using information inherent to a living body, such as fingerprint authentication, face image authentication, iris authentication, vein authentication and the like has been generally known.

Patent Document 1 discloses a biological information measurement device configured to authenticate a wearer by using a vein pattern.

Patent Document 2 discloses a health condition monitoring device that is configured to perform both face authentication and voiceprint authentication for a target person, to determine authentication success when at least one authentication is successful, and to start examination on a health condition of the target person.

Patent Document 3 discloses a system configured to discount an insurance fee of an insured person on the basis of biological information of the insured person. In the system, an exercise condition monitoring device that is worn on the insured person is configured to check whether the device is worn and to perform identity verification by using a question, a password, a fingerprint, a voiceprint, an electrocardiographic waveform, a heartbeat and the like, at a timing at which it is detected that the wearer has stopped the exercise. When the check and the verification are made, the exercise condition monitoring device stores the measured exercise performance information, as effective information. According to this configuration, it is possible to prevent the insurance fee of the insured person from being determined in a state where the exercise condition monitoring device is used by another person other than the insured person.

Patent Document 1: JP-A-2013-212315
Patent Document 2: JP-A-2012-10955
Patent Document 3: JP-A-2002-238877

As devices requiring personal authentication, a biological information measurement device configured to continuously measure blood pressure information such as a systolic arterial pressure, a diastolic pressure or a pulse pressure, pulse information such as a pulse rate, heartbeat information such as a heart rate, and the like may be exemplified. The biological information measurement device is used at home by a measurement subject who has had a medical examination in a hospital, for example. Considering the using aspect, it is important for the medical examination that the biological information to be measured by the biological information measurement device is measured from the measurement subject.

Also, in the case of a service of determining an insurance fee of a hospitalization insurance, a life insurance or the like of the measurement subject on the basis of the blood pressure information and the like continuously measured from the measurement subject, it is necessarily required that the biological information to be measured by the biological information measurement device should be securely measured from the measurement subject.

As disclosed in Patent Document 1, when the biological information measurement device is configured to detect the vein pattern only in a state where it is worn on the living body, it is possible to achieve an effect of preventing impersonation of a third party. However, since this configuration requires a research to avoid interference with other device (for example, a pulse wave detection sensor) configured to measure the biological information, the manufacturing cost of the biological information measurement device increases and the downsizing of the biological information measurement device is hindered.

In the meantime, in a configuration where a finger is put into the device from an outside for detecting the vein pattern with the device being worn on the living body, it is possible to avoid the interference with the other device. However, according to this configuration, it is difficult to prevent the impersonation.

As disclosed in Patent Document 2, in the case of the device configured to perform the identity verification of the target person by the face authentication and the voiceprint authentication, the target person has to be in the vicinity of the device only when the health condition examination starts, so that a health condition of a person different from the target person may be examined. For this reason, it is difficult to prevent the impersonation of the third party.

As disclosed in Patent Document 3, according to the method of performing the identity verification at a timing at which the motion of the measurement subject wearing the device has stopped, the identity verification is performed at random timings. For this reason, in order to carry out a fraud that a third party different from the authorized user wears the device and the authorized user operates the device to make a success of the identity verification only when the identity verification is performed, the third party and the authorized user should move together all the time. However, since it is not realistic for the two persons to move together all the time, it is possible to prevent the impersonation of the third party.

The device disclosed in Patent Document 3 may perform the identity verification at the plurality of timings during the wearing. However, in real life, it is assumed that the measurement subject may not perform the operation for the identity verification during driving of a vehicle and working and the like. In this case, the identity verification is determined to be failure, so that the exercise performance information measured up to the timing at which the identity verification is performed may be invalidated.

The present invention has been made in view of the above situations, and is to provide a biological information measurement device and a method for determining correctness of biological information capable of sufficiently storing biological information to be measured from an authorized user while preventing impersonation of a user.

SUMMARY

A biological information measurement device of the present invention is a biological information measurement device configured to continuously measure biological information from a living body with being worn on the living body, and includes a storage control unit configured to perform storage control of the measured biological information in a storage medium, an input unit for inputting identification information necessary for personal identification, an information input request unit configured to request an input of the identification information by the input unit at each of a plurality of timings after measurement of the biological information is started, a personal identification unit configured to determine whether a user wearing the biological information measurement device is a pre-registered person in synchronization with each of the plurality of timings, based on the identification information input by the input unit, an identification result information generation unit configured to generate identification result information indicative of a relationship between a first number of times that the request is made by the information input request unit and a second number of times that the user is determined to be the pre-registered person by the personal identification unit, and a correctness determination unit configured to determine correctness of the biological information stored in the storage medium on the basis of the identification result information.

A method for determining correctness of biological information of the present invention is a method for determining correctness of biological information stored in a storage medium by a biological information measurement device configured to continuously measure the biological information from a living body with being worn on the living body, and includes an information input request step of requesting an input of identification information by an input unit provided in the biological information measurement device for inputting the identification information necessary for personal identification, at each of a plurality of timings after measurement of the biological information is started by the biological information measurement device, a personal identification step of determining whether a user wearing the biological information measurement device is a pre-registered person in synchronization with each of the plurality of timings, based on the identification information input by the input unit, an identification result information generation step of generating identification result information indicative of a relationship between a first number of times that the request is made in the information input request step and a second number of times that the user is determined to be the pre-registered person in the personal identification step, and a correctness determination step of determining correctness of the biological information stored in the storage medium on the basis of the identification result information.

DESCRIPTION OF EXEMPLARY EMBODIMENTS

Hereinafter, an illustrative embodiment of the present invention will be described with reference to the drawings.

Figure 1:
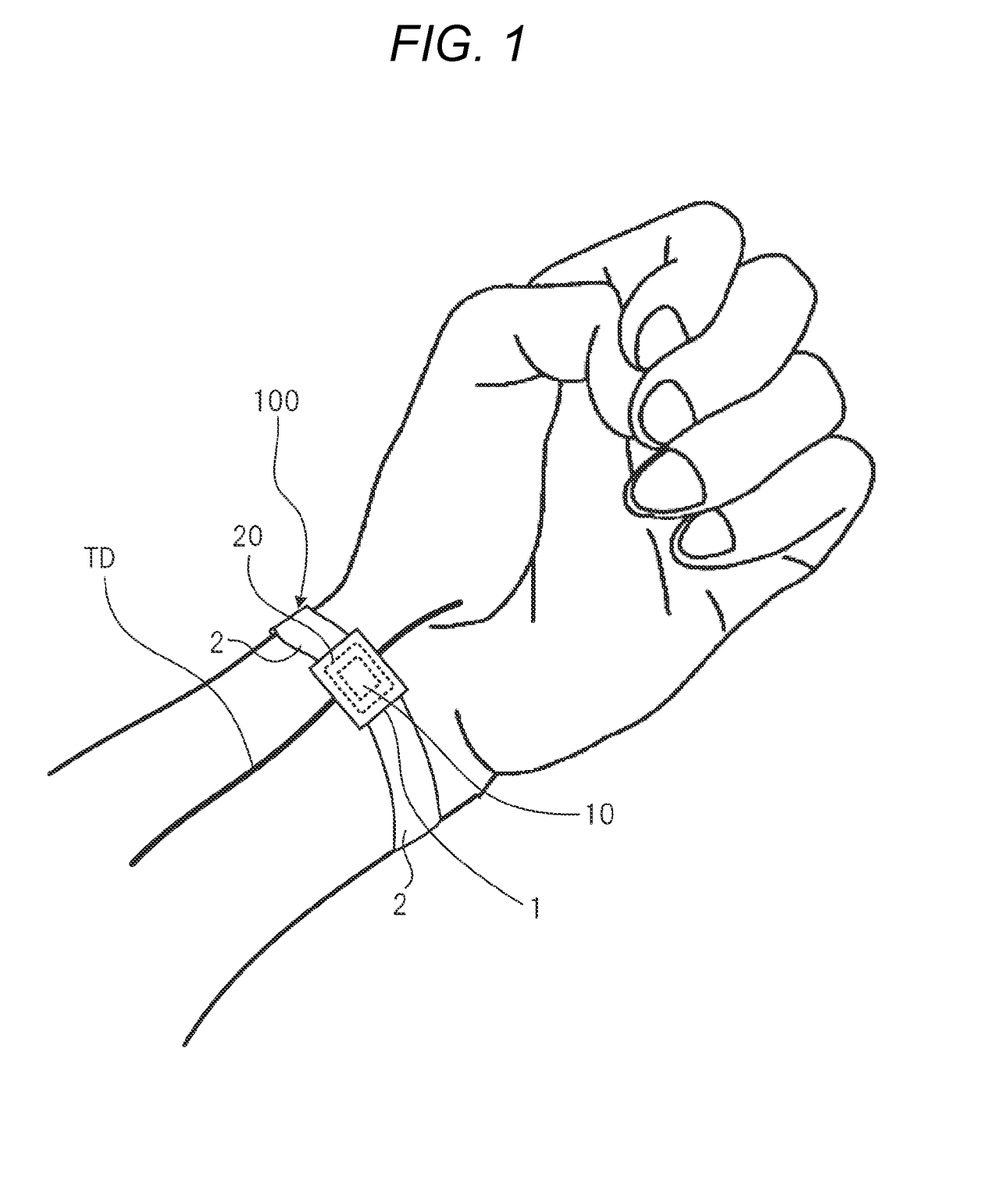
FIG. 1 is a pictorial view depicting a schematic configuration of an outer shape of a biological information measurement device 100 for illustrating an illustrative embodiment of the present invention.

FIG. 1 is a pictorial view depicting a schematic configuration of an outer shape of a biological information measurement device 100 for illustrating an illustrative embodiment of the present invention.

The biological information measurement device 100 includes a main body unit 1 and a belt 2 fixed to the main body unit 1. The biological information measurement device 100 is used with being worn on a wrist having skin below which a radial artery TD, which is a measurement target of the biological information, exists, and is used with the main body unit 1 being worn on the wrist by the belt 2. The biological information, which is a measurement target of the biological information measurement device 100, includes blood pressure information such as a systolic arterial pressure, a diastolic pressure, a pulse pressure or the like, pulse information such as a pulse rate, vascular property information such as AI (Augmentation Index), PTT (pulse wave velocity) or the like, heartbeat information such as a heart rate, and the like.

The main body unit 1 of the biological information measurement device 100 includes a pressure sensor 10 for detecting a pressure pulse wave from the radial artery TD and a pressing mechanism 20 for pressing the pressure sensor 10 to the wrist.

Figure 2:
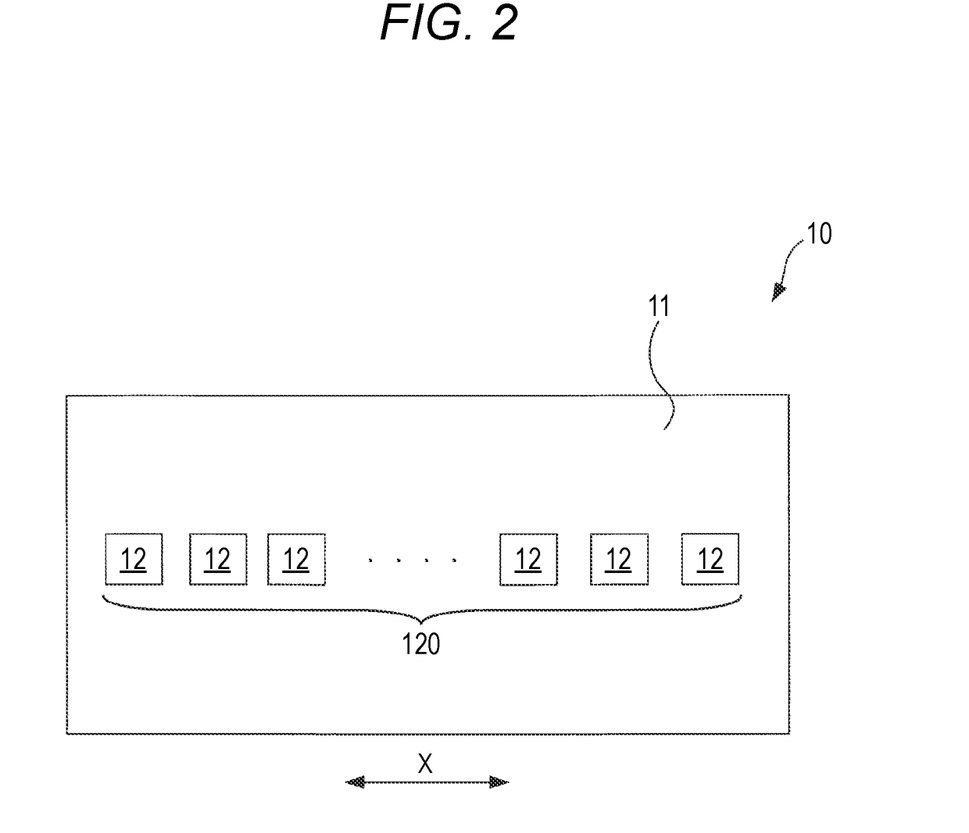
FIG. 2 is a pictorial plan view depicting a pressure sensor 10 of the biological information measurement device 100 shown in FIG. 1, as seen from a contact surface with a wrist.

FIG. 2 is a pictorial plan view depicting the pressure sensor 10 of the biological information measurement device 100 shown in FIG. 1, as seen from a contact surface with the wrist. As shown in FIG. 2, the pressure sensor 10 includes an element row 120 formed on a base body 11 having a flat plate shape.

The element row 120 is configured by a plurality of pressure detection elements 12 aligned in a direction X, which is one direction. As the pressure detection element 12, an element configured to detect a pressure and to convert the same into an electric signal may be used. For example, an element using a piezo resistance effect is used.

An interval of the plurality of pressure detection elements 12 in the alignment direction is sufficiently small so that the necessary number of the pressure detection elements are to be arranged above the radial artery TD. A distance of the pressure detection elements, which are located at both end portions, of the plurality of pressure detection elements 12 is set to be sufficiently greater than a diameter size of the radial artery TD.

The pressure sensor 10 is pressed to the wrist by the pressing mechanism 20 in a state where the direction X, which is the alignment direction of the plurality of pressure detection elements 12 included in the element row 120, intersects with a direction in which the radial artery TD extends. In the meantime, the pressure sensor 10 may have a configuration where a plurality of the element rows 120 is aligned on the base body 11 in a direction perpendicular to the direction X.

Figure 3:
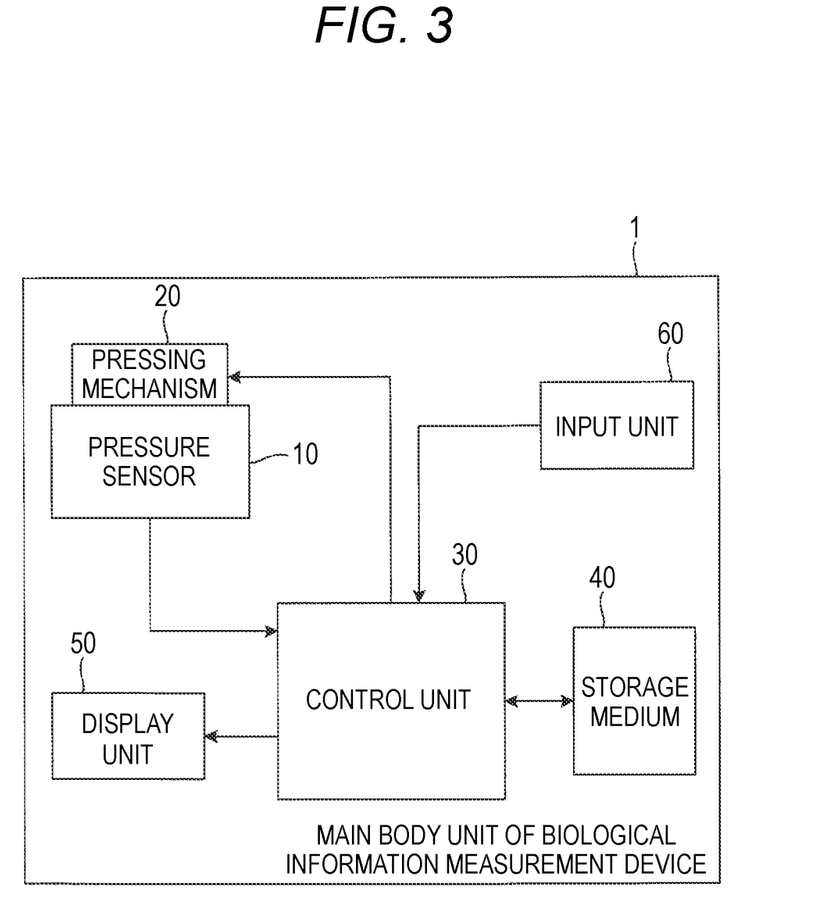
FIG. 3 depicts an internal hardware configuration of a main body unit 1 of the biological information measurement device 100 shown in FIG. 1.

FIG. 3 depicts an internal hardware configuration of the main body unit 1 of the biological information measurement device 100 shown in FIG. 1.

The main body unit 1 includes the pressure sensor 10, the pressing mechanism 20, a control unit 30 configured to collectively control the entire device, a storage medium 40, a display unit 50, and an input unit 60.

The pressing mechanism 20 includes an air bag fixed to a surface opposite to a surface, on which the element row 120 is formed, of the base body 11 and a pump configured to regulate an internal pressure of the air bag, for example. A pressing force (an internal pressure of the pump) to the wrist by the pressing mechanism 20 is controlled by the control unit 30. As the pressing mechanism 20, any mechanism capable of pressing the pressure sensor 10 to the wrist can be used. That is, the present invention is not limited to the mechanism using the air bag.

The pressure sensor 10 is configured to input a pressure signal, which is detected by each pressure detection element 12 configuring the element row 120, to the control unit 30.

The control unit 30 includes a ROM (Read Only Memory), a RAM (Random Access Memory), and a processor, and is configured to collectively control the entire main body unit 1 as the processor executes programs stored in the ROM. The programs include a program for determining correctness of biological information. The RAM functions as a work memory when the control unit 30 executes a variety of processing.

The storage medium 40 is a medium to and from which data can be stored and read out, and a flash memory or the like is used, for example. As the storage medium 40, a portable medium such as a memory card may be used, or a medium that is fixed to the main body unit 1 and cannot be taken out may also be used.

The display unit 50 is to display a variety of information including the biological information, and is configured by a liquid crystal display device, for example.

The input unit 60 is a device for inputting information (hereinafter, referred to as "identification information") necessary for personal identification. The identification information is information inherent to a living body, such as fingerprint information, voiceprint information, face image information, iris information, vein information and the like.

Figure 4:
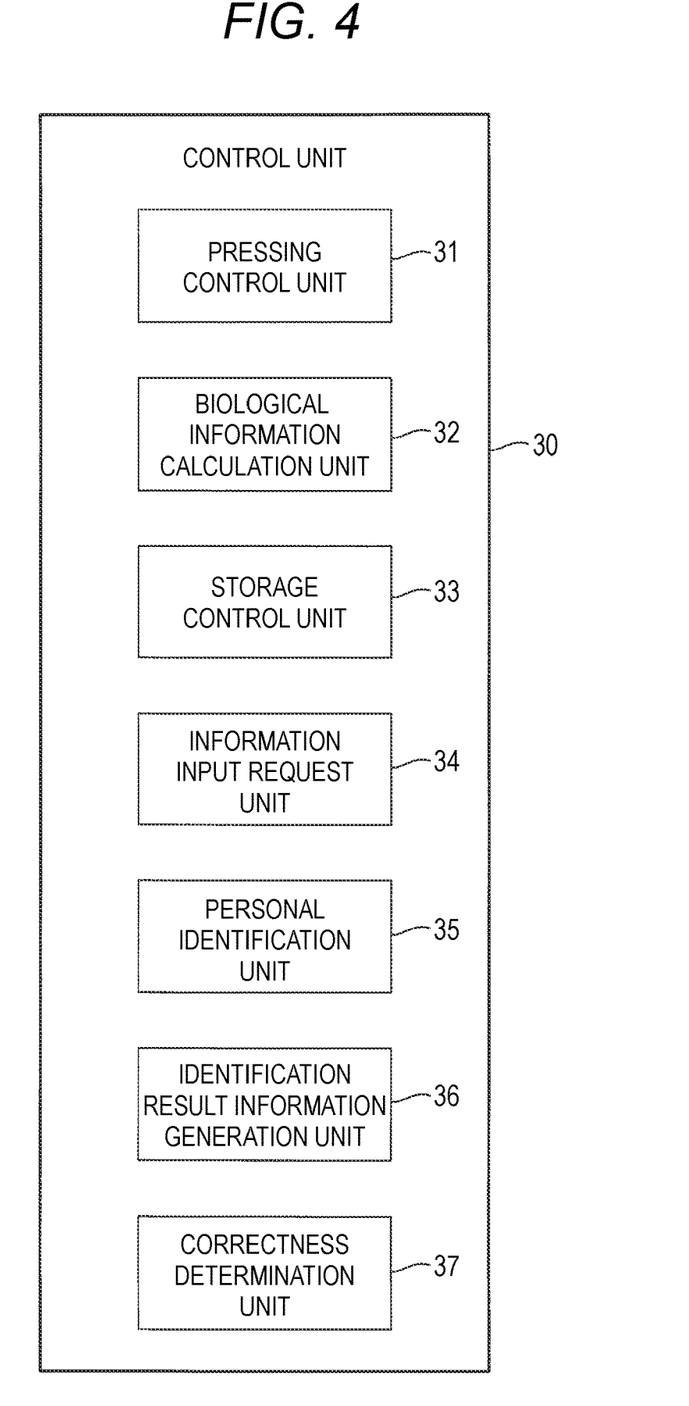
FIG. 4 is a functional block diagram of a control unit 30 shown in FIG. 3.

FIG. 4 is a functional block diagram of the control unit 30 shown in FIG. 3.

The control unit 30 is configured to execute the programs stored in the ROM, thereby functioning as a pressing control unit 31, a biological information calculation unit 32, a storage control unit 33, an information input request unit 34, a personal identification unit 35, an identification result information generation unit 36 and a correctness determination unit 37.

The pressing control unit 31 is configured to drive the pressing mechanism 20, thereby controlling the pressing force of the pressure sensor 10 to the wrist by the pressing mechanism 20.

The biological information calculation unit 32 is configured to calculate the biological information such as the blood pressure information, the pulse information, the heartbeat information or the like every each pulse or every several pulses, based on the information of the pressure pulse wave detected by the optimal pressure detection element of the plurality of pressure detection elements 12 configuring the element row 120 in a pressing state where the pressure sensor 10 is pressed to the wrist with an optimal pressing force by the pressing mechanism 20.

The optimal pressing force is a pressing force capable of implementing a state in which the pressure pulse wave can be detected without being influenced by circumferential tension of a blood vessel from the radial artery TD pressed by the optimal pressing force, i.e., a tonometry state. The optimal pressure detection element indicates the pressure detection element 12 located immediately above the radial artery TD pressed and flattened with the optimal pressing force by the pressure sensor 10.

The storage control unit 33 is configured to perform control of storing the biological information calculated by the biological information calculation unit 32 in the storage medium 40.

The information input request unit 34 is configured to request an input of the identification information by the input unit 60 at each of a plurality of timings after measurement of the biological information is started by the biological information measurement device 100.

The timing at which the information input request unit 34 requests the input of the identification information is set to a random timing determined by a random number.

The personal identification unit 35 is configured to determine whether the user wearing the biological information measurement device 100 is a pre-registered user (an authorized user of the biological information measurement device 100) in synchronization with each of the plurality of timings, based on the identification information input by the input unit 60.

For example, in the case that the input unit 60 is a device configured to input the fingerprint information, the fingerprint information of an authorized user of the biological information measurement device 100 stored in advance in the storage medium 40 and the fingerprint information input from the input unit 60 are compared, and when a degree of coincidence of the two fingerprint information is equal to or higher than a threshold value, the user wearing the biological information measurement device 100 is determined to be the authorized user. In this way, the well-known method can be used as the method of determining whether the user is an authorized user.

The identification result information generation unit 36 is configured to generate identification result information indicative of a relationship between a first number of time that the request is made by the information input request unit 34 and a second number of times that the user wearing the biological information measurement device 100 is determined to be the authorized user by the personal identification unit 35.

The identification result information is a ratio of the second number of times to the first number of times (hereinafter, referred to as "authentication success rate", a ratio of a third number of times, which is obtained by subtracting the second number of times from the first number of times, to the first number of times (hereinafter, referred to as "authentication failure rate") or the like.

The correctness determination unit 37 is configured to determine correctness of the biological information stored in the storage medium 40, based on the identification result information generated by the identification result information generation unit 36. The determination of the correctness of the biological information means determining whether the biological information has been measured from the pre-registered authorized user.

In the storage medium 40 of the biological information measurement device 100, identification information for identifying the authorized user who has been requested to use the biological information measurement device 100 from a doctor, an insurance company and the like is stored. The biological information measurement device 100 is provided with a user registration mode in which the identification information is to be stored in the storage medium 40.

In the below, operations of the biological information measurement device 100 that are to be executed when the user registration mode is set are described.

When an instruction to register a user is issued by a button operation or the like, the control unit 30 requests an input of the identification information, stores the identification information, which is input from the input unit 60 in response to the request, in the storage medium 40 in association with an authorized ID indicative of the authorized user, and ends the user registration mode. From the series of processing, a specific user is registered as the authorized user in the biological information measurement device 100.

Figure 5:
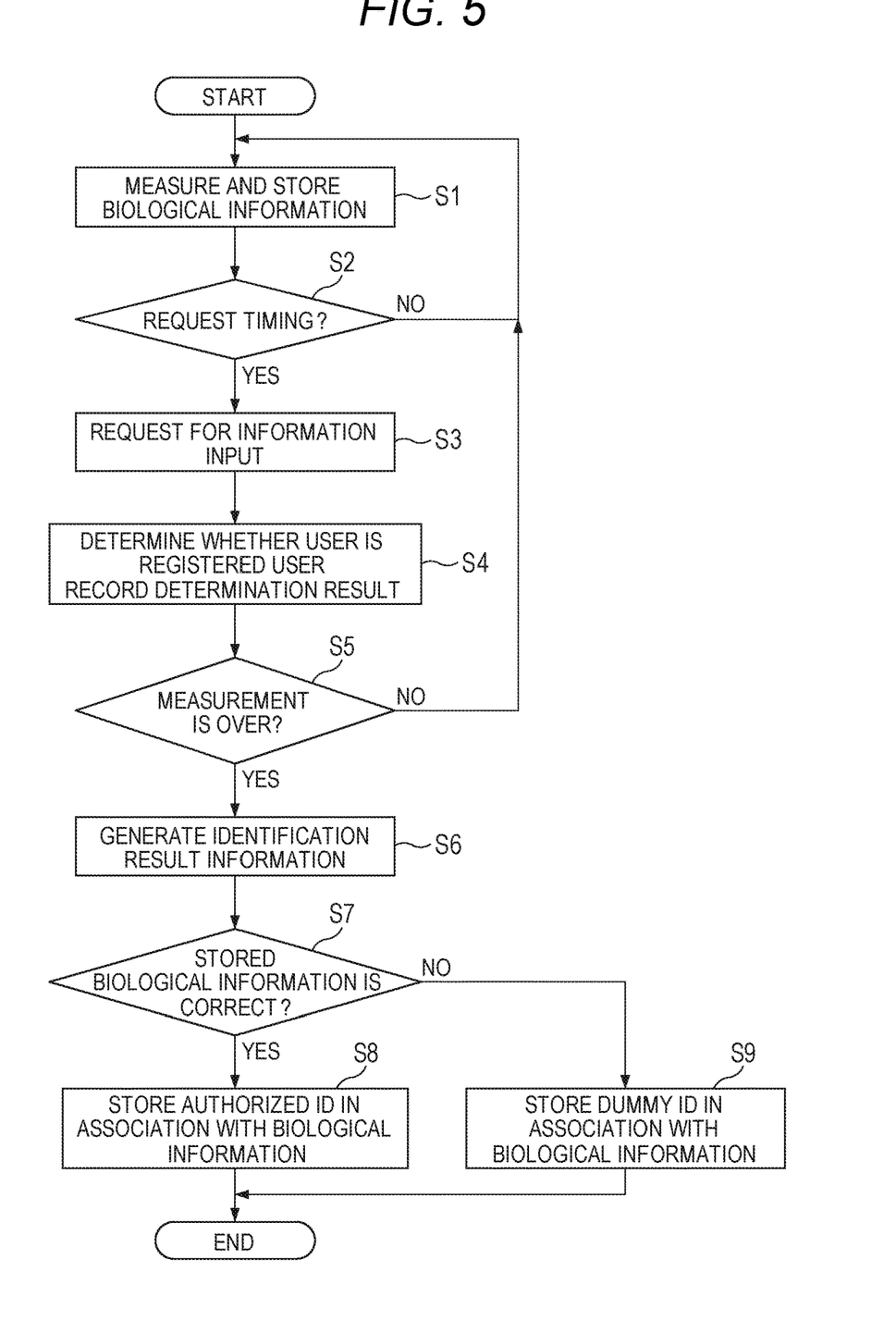
FIG. 5 is a flowchart for illustrating operations of the biological information measurement device 100 shown in FIG. 1 during a biological information measurement mode.

FIG. 5 is a flowchart for illustrating operations of the biological information measurement device 100 shown in FIG. 1 during a biological information measurement mode.

When a measurement subject wears the biological information measurement device 100 on the wrist and pushes a measurement start button (not shown) provided to the biological information measurement device 100, a signal instructing start of measurement of the biological information is input to the control unit 30, so that the flow shown in FIG. 5 starts.

When the signal instructing start of measurement of the biological information is input to the control unit 30, the pressing force to the wrist by the pressing mechanism 20 is controlled by the pressing control unit 31. In this state, the biological information calculation unit 32 calculates the biological information, based on the pressure pulse wave detected from the optimal pressure detection element of the pressure sensor 10, and stores the calculated biological information in the storage medium 40 in association with information of detection date and time of the pressure pulse wave (step S1).

Then, the information input request unit 34 determines whether it is a timing at which an input of the identification information is to be requested (step S2). When it is not a timing at which an input of the identification information is to be requested (step S2: NO), the processing returns to step S1.

When it is a timing at which an input of the identification information is to be requested (step S2: YES), the information input request unit 34 requests an input of identification information (step S3).

For example, the information input request unit 34 displays, on the display unit 50, message information for requesting an input of the identification information, such as "The fingerprint authentication starts. Please touch a finger to the fingerprint sensor.", "The face authentication (iris authentication) starts. Please turn your face to the camera." or "The voiceprint authentication starts. Please speak "OO" toward the microphone." In addition to the display of the message information, a sound may be output from a speaker (not shown) or a vibrator (not shown) may be operated to vibrate the device so that the user can easily perceive the message information.

Also, the information input request unit 34 may output the message information by a voice from the speaker, instead of displaying the message information on the display unit 50.

When the user inputs the identification information by the input unit 60, in response to the message information output in this way, the personal identification unit 35 determines whether the user wearing the biological information measurement device 100 is the registered user (authorized user), based on the identification information input from the input unit 60 and the identification information corresponding to the authorized ID stored in the storage medium 40, and stores a determination result in the storage medium 40 (step S4).

Specifically, when a degree of coincidence of the two identification information is equal to or higher than a threshold value, the personal identification unit 35 determines that the user wearing the biological information measurement device 100 is the registered user (authorized user), and stores information indicative of an authentication success, which is a determination result, in the storage medium 40 in association with date and time.

When the degree of coincidence of the two identification information is lower than the threshold value, the personal identification unit 35 determines that the user wearing the biological information measurement device 100 is not the registered user (authorized user), and stores information indicative of an authentication failure, which is a determination result, in the storage medium 40 in association with date and time.

Also, when the identification information is not input by the input unit 60 after the information input request unit 34 requests the input of the identification information until predetermined time such as 10 seconds elapses, the personal identification unit 35 stores the information indicative of an authentication failure, which is a determination result, in the storage medium 40 in association with date and time.

After step S4, the control unit 30 determines whether an instruction to end the measurement of the biological information is issued by an operation of a measurement ending button (not shown) (step S5). When there is no instruction (step S5: NO), the control unit returns to step S1.

When there is an instruction (step S5: YES), the identification result information generation unit 36 generates identification result information, based on the information indicative of the determination result made by the personal identification unit 35 and stored in the storage medium 40 (step S6).

Specifically, the identification result information generation unit 36 counts total numbers of the information indicative of an authentication success and the information indicative of an authentication failure associated with dates and times of a time period after the instruction to start the measurement of the biological information is issued until the instruction to end the measurement of the biological information is issued.

The identification result information generation unit 36 adds the total number N1 of the information indicative of an authentication success and the total number N2 of the information indicative of an authentication failure, thereby calculating the number of times N3 that the request for the input of the identification information is made by the information input request unit 34 during the time period. In the meantime, since the number of times N3 is a numerical value perceived by the information input request unit 34, it may be acquired from the information input request unit 34.

The identification result information generation unit 36 generates an authentication success rate (unit: %) indicative of a ratio of the total number N1 to the number of times N3 or an authentication failure rate (unit: %) indicative of a ratio of the total number N2 to the number of times N3, as the identification result information.

When the identification result information is generated in step S6, the correctness determination unit 37 determines the correctness of the biological information, which corresponds to the date and time of the time period, of the biological information stored in the storage medium 40, based on the identification result information (step S7).

In the case where the identification result information is the authentication success rate, the correctness determination unit 37 determines that the biological information corresponding to the date and time of the time period stored in the storage medium 40 is correct, if the authentication success rate exceeds a first preset threshold value, and determines that the biological information corresponding to the date and time of the time period stored in the storage medium 40 is incorrect, if the authentication success rate is equal to or smaller than the first preset threshold value.

As the first threshold value, a value smaller than 100% is set. If the first threshold value is too small, the reliability of the correctness determination result is lowered. Therefore, the first threshold value is preferably set to a value greater than 50%, more preferably a value equal to or greater than 70%, and most preferably a value equal to or greater than 90%.

In the case where the identification result information is the authentication failure rate, the correctness determination unit 37 determines that the biological information corresponding to the date and time of the time period stored in the storage medium 40 is correct, if the authentication failure rate is smaller than a second preset threshold value, and determines that the biological information corresponding to the date and time of the time period stored in the storage medium 40 is incorrect, if the authentication failure rate is equal to or greater than the second preset threshold value.

As the second threshold value, a value greater than 0% is set. If the second threshold value is too large, the reliability of the correctness determination result is lowered. Therefore, the second threshold value is preferably set to a value smaller than 50%, more preferably a value equal to or smaller than 30%, and most preferably a value equal to or smaller than 10%.

In step S7, when it is determined that the biological information corresponding to the date and time of the time period is correct (step S7: YES), the storage control unit 33 stores the biological information that has been determined to be correct in the storage medium 40 in association with the authorized ID (step S8).

In step S7, when it is determined that the biological information corresponding to the date and time of the time period is incorrect (step S7: NO), the storage control unit 33 stores the biological information that has been determined to be incorrect in the storage medium 40 in association with a dummy ID different from the authorized ID (step S9).

As described above, according to the biological information measurement device 100, the processing of step S3 is randomly executed and the determination result made by the personal identification unit 35 is stored in the storage medium 40. Then, the correctness of the biological information is determined by the identification result information generated on the basis of the determination result.

For this reason, in order to carry out a fraud that a third party different from the authorized user wears the biological information measurement device 100 and the authorized user operates the input unit 60 to make a success of the authentication only when the processing of step S3 is performed, the third party and the authorized user should move together all the time. However, since it is not realistic for the two persons to move together all the time, it is possible to prevent the impersonation of the third party.

Also, according to the biological information measurement device 100, since the correctness of the biological information is determined on the basis of the value of the authentication success rate or the authentication failure rate, even when there are several cases where the authorized user cannot respond to the request made in step S3 due to diverse reasons such as driving of a vehicle, working and the like, it is not determined that the biological information is incorrect. Therefore, it is possible to store the biological information measured from the authorized user in association with the authorized ID without waste.

Also, according to the biological information measurement device 100, as the input unit 60, it is possible to select an input unit, which is inexpensive and can be downsized, considering the manufacturing cost and size of the device, so that it is possible to downsize the biological information measurement device 100 at low cost.

In the above, the timing at which the processing of step S3 is executed is a random timing determined by a random number. However, the present invention is not limited thereto.

For example, the information input request unit 34 may request the input of the identification information at a timing at which the biological information calculated by the biological information calculation unit 32 exceeds a threshold value, at a timing based on a signal received from an external apparatus such as a server that is managed by a manager who manages the biological information measurement device 100 or at a timing at which an amount of change (a value obtained by subtracting the biological information corresponding to old date and time from the biological information corresponding to new date and time) of the calculated biological information exceeds a threshold value.

According to the above configuration, like the configuration where the random number is used, since the wearer and the like cannot know the timing at which the processing of step S3 is to be executed, it is possible to achieve the impersonation prevention effect. In the configuration where the information input request unit 34 requests the input of the identification information at timing based on a signal received from an external apparatus, the main body unit 1 of the biological information measurement device 100 is provided with a communication interface for performing communication with the external apparatus, and when the communication interface receives a signal to instruct the request for the input of the identification information, the information input request unit 34 requests the input of the identification information. Thereby, the manager can request the input of the identification information at any timing and a system can be established in accordance with the manager's request.

Also, the information input request unit 34 may request the input of the identification information at a timing at which environment information around the biological information measurement device 100 has changed beyond a threshold value.

The environment information is information of a temperature or humidity of an environment in which the biological information measurement device 100 is put or information of a level of a sound around the biological information measurement device 100, for example.

It may be determined whether the temperature or humidity has changed beyond the threshold value, based on information from a temperature sensor or a humidity sensor provided to the biological information measurement device 100.

It may be determined whether the level of the sound has changed, based on a level of a sound detected by a microphone provided to the biological information measurement device 100.

According to the above configuration, the processing of step S3 is executed at a timing at which the user wearing the biological information measurement device 100 goes out of user's home or gets on a train at a platform of a station. In this way, the request for the input of the identification information is made at the timing at which the user moves. Accordingly, the user and the third party who attempt the fraud should move together all the time, so that it is possible to achieve the impersonation prevention effect.

Also, the information input request unit 34 may request the input of the identification information at a timing at which an operation of the user wearing the biological information measurement device 100 has stopped.

The operation of the user is detected by detection information of a body motion detection unit such as an acceleration sensor provided to the biological information measurement device 100. When the operation of the user almost stops during preset time, the information input request unit 34 executes the processing of step S3, based on the detection information of the body motion detection unit.

According to the above configuration, the processing of step S3 is executed while the user wearing the biological information measurement device 100 repeats the motion and stop. Like this, the request for the input of the identification information is made while the user repeats the motion and stop, which are frequently performed in the daily life. Accordingly, the user and the third party who attempt the fraud should move together all the time, so that it is possible to achieve the impersonation prevention effect.

Figure 6:
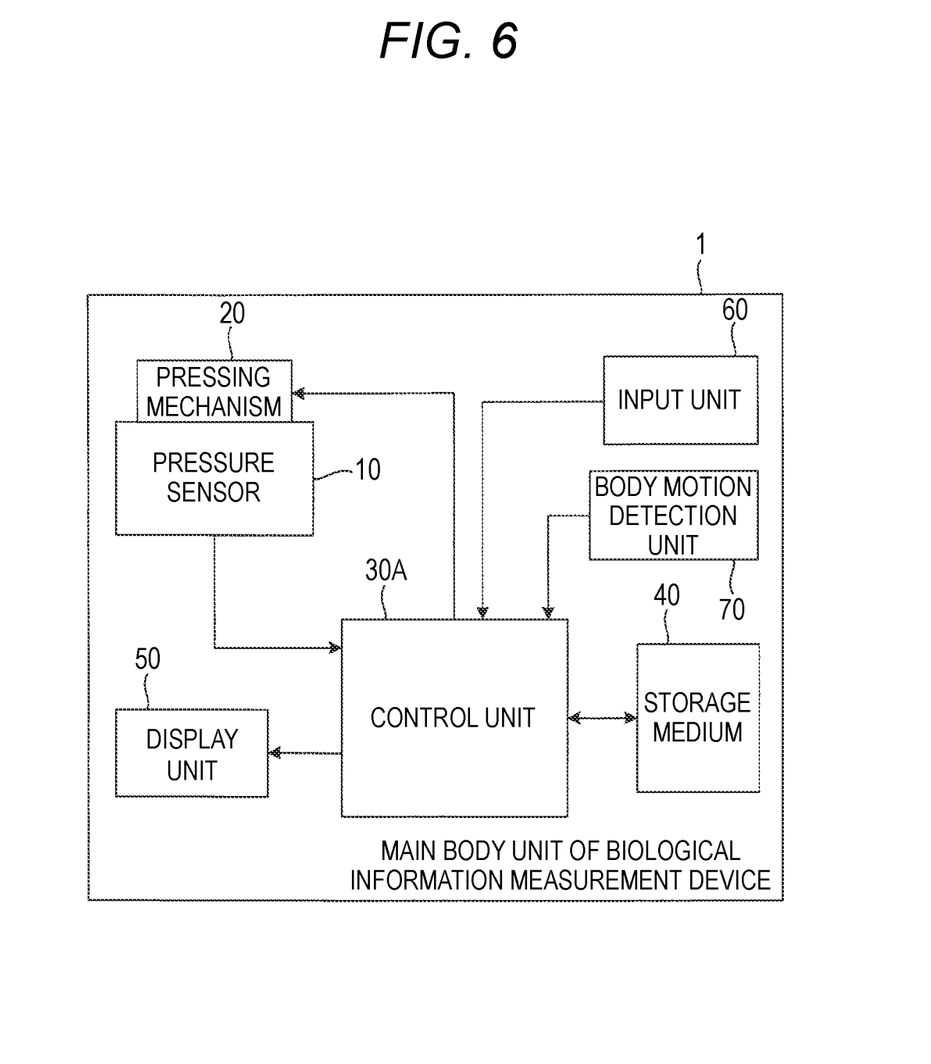
FIG. 6 depicts a modified embodiment of the internal hardware configuration of the main body unit 1 of the biological information measurement device 100 shown in FIG. 3.

FIG. 6 depicts a modified embodiment of the internal hardware configuration of the main body unit 1 of the biological information measurement device 100 shown in FIG. 3. The main body unit 1 shown in FIG. 6 has the same configuration as that shown in FIG. 3, except that a body motion detection unit 70 is added and the control unit 30 is replaced with a control unit 30A. In FIG. 6, the same configurations as FIG. 3 are denoted with the same reference numerals, and the descriptions thereof are omitted.

The body motion detection unit 70 is configured to detect body motion of the user wearing the biological information measurement device 100 by an acceleration sensor, an angular velocity sensor, a pneumatic sensor and the like.

Figure 7:
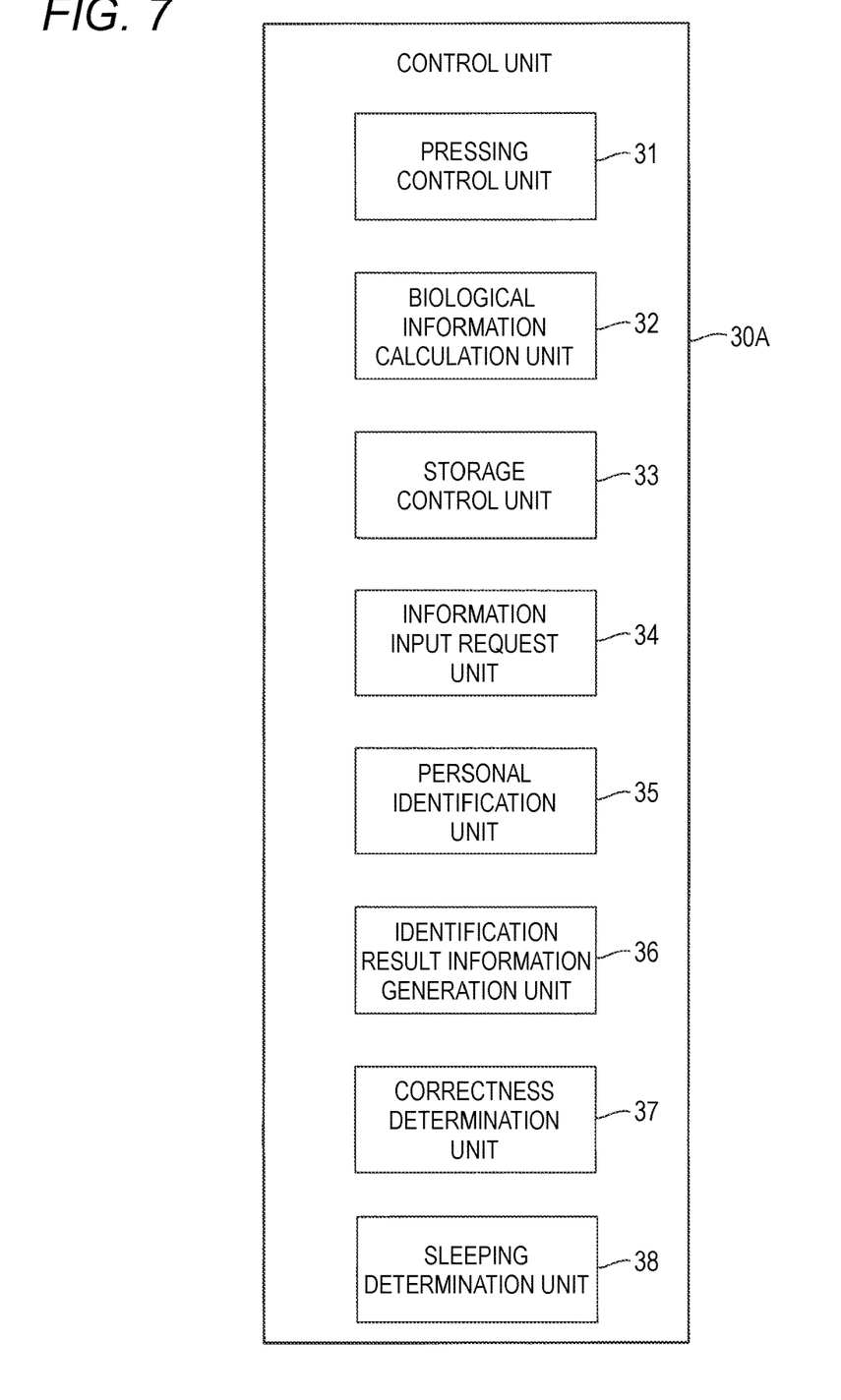
FIG. 7 is functional block diagram of a control unit 30A shown in FIG. 6.

FIG. 7 is a functional block diagram of the control unit 30A shown in FIG. 6. The control unit 30A shown in FIG. 7 has the same configuration as the control unit 30 of FIG. 4, except that a sleeping determination unit 38 is added. In FIG. 7, the same configurations as FIG. 4 are denoted with the same reference numerals, and the descriptions thereof are omitted.

The sleeping determination unit 38 is configured to determine whether the user wearing the biological information measurement device 100 is sleeping, based on the body motion information detected by the body motion detection unit 70.

Figure 8:
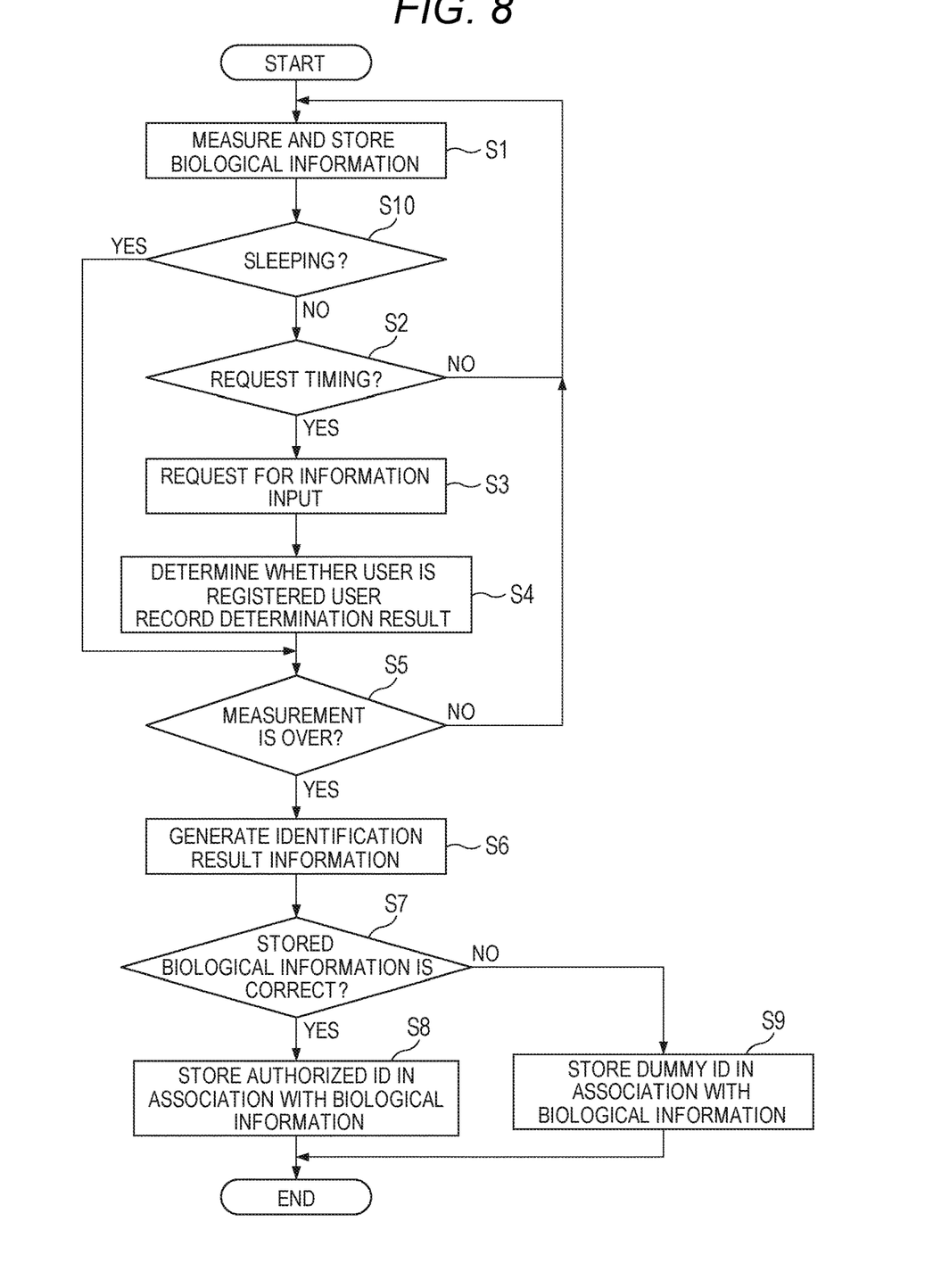
FIG. 8 is a flowchart for illustrating operations of the biological information measurement device 100 including the main body unit 1 shown in FIG. 6 during the biological information measurement mode.

FIG. 8 is a flowchart for illustrating operations of the biological information measurement device 100 including the main body unit 1 shown in FIG. 6 during the biological information measurement mode. In FIG. 8, the same processing as FIG. 5 is denoted with the same reference numerals, and the descriptions thereof are omitted.

After step S1, the sleeping determination unit 38 determines whether the user wearing the biological information measurement device 100 is sleeping, based on the body motion information detected by the body motion detection unit 70 (step S10).

When it is determined that the user is sleeping (step S10: YES), the processing of step S5 is executed. When it is determined that the user is not sleeping (step S10: NO), the processing of step S2 and thereafter is executed.

As described above, while the user wearing the biological information measurement device 100 is sleeping, the processing of steps S2 to step S4 is omitted. According to this configuration, it is possible to extremely reduce the possibility that the user cannot respond to the request made in step S3, and it is possible to prevent the dummy ID from being associated with the biological information measured from the authorized user. Also, during the sleeping, the processing of step S3 is not executed, so that it is possible to support the sound sleep of the user.

In the operation examples shown in FIGS. 5 and 8, the processing of step S6 and thereafter is executed at the timing at which the control unit 30 or the control unit 30A receives the instruction to end the measurement of the biological information.

The timing at which the processing of step S6 and thereafter is executed may be preset time such as 24-hour indicative of the end of one day.

In this case, the correctness determination unit 37 determines the correctness of the biological information, for which the correctness determination has not been performed, of the biological information stored in the storage medium 40 after the measurement of the biological information is started until the corresponding time, based on the identification result information.

According to the above configuration, even when the user continues to wear the biological information measurement device 100 for several days, the processing of step S6 to step S9 is periodically executed. In this way, the processing of step S6 to step S9 is executed every predetermined day, so that it is possible to reduce the variation of the number of request times of the identification information, which is a basis of the calculation of the authentication success rate or the authentication failure rate, so that it is possible to stabilize the accuracy of the correctness determination.

Also, the correctness determination unit 37 may be configured to select and set the first threshold value or the second threshold value, which is to be compared with the identification result information, from a plurality of values.

For example, when using the biological information measurement device 100 for diagnosis in a hospital, it is thought that the impersonation possibility is low. For this reason, in this case, the first threshold value is preferably set to a slightly small value, or the second threshold value is preferably set to a slightly large value.

On the other hand, when using the biological information measurement device 100 for determining an insurance fee, it is thought that the impersonation possibility is high. For this reason, in this case, the first threshold value is preferably set to a slightly large value, or the second threshold value is preferably set to a slightly small value.

The correctness determination program is recorded in a non-transitory storage medium from which a computer can read the correctness determination program.

The "computer-readable storage medium" includes an optical medium such as a CD-ROM (Compact Disc-ROM), a magnetic recording medium such as a memory card, and the like, for example. Also, the program may be provided by a downloading through a network.

The disclosed illustrative embodiments are exemplary in every respect and should not be construed as being limited. The scope of the present invention is defined in the claims, not in the above description, and includes all changes within the meaning and scope equivalent to the claims.

For example, in the above, the biological information measurement device 100 is configured to measure the biological information on the basis of the pressure pulse wave detected by the pressure sensor 10 but may be configured to measure the biological information on the basis of a pulse wave detected by a photoelectric pulse wave sensor. Alternatively, the biological information measurement device may be configured to measure the biological information by a cuff and a pressure sensor configured to detect an internal pressure of the cuff.

The biological information measurement device 100 is configured to measure the biological information every each pulse or every several pulses but may be configured to measure and store the biological information at a preset time interval such as every 30 minutes or every one hour. Like this, the present invention is useful for the biological information measurement device configured to continuously measure and store the biological information from the living body.

As described above, the specification discloses following items.

The disclosed biological information measurement device is a biological information measurement device configured to continuously measure biological information from a living body with being worn on the living body, and includes a storage control unit configured to perform storage control of the measured biological information in a storage medium, an input unit for inputting identification information necessary for personal identification, an information input request unit configured to request an input of the identification information by the input unit at each of a plurality of timings after measurement of the biological information is started, a personal identification unit configured to determine whether a user wearing the biological information measurement device is a pre-registered person in synchronization with each of the plurality of timings, based on the identification information input by the input unit, an identification result information generation unit configured to generate identification result information indicative of a relationship between a first number of times that the request is made by the information input request unit and a second number of times that the user is determined to be the pre-registered person by the personal identification unit, and a correctness determination unit configured to determine correctness of the biological information stored in the storage medium on the basis of the identification result information.

In the disclosed biological information measurement device, the identification result information is a ratio of the second number of times to the first number of times, and when the ratio exceeds a threshold value, the correctness determination unit determines that the biological information stored in the storage medium is correct, and when the ratio is equal to or smaller than the threshold value, the correctness determination unit determines that the biological information stored in the storage medium is incorrect.

In the disclosed biological information measurement device, the identification result information is a ratio of a third number of times, which is obtained by subtracting the second number of times from the first number of times, to the first number of times, and when the ratio is smaller than a threshold value, the correctness determination unit determines that the biological information stored in the storage medium is correct, and when the ratio is equal to or greater than the threshold value, the correctness determination unit determines that the biological information stored in the storage medium is incorrect.

In the disclosed biological information measurement device, the threshold value is selected and used from a plurality of values.

In the disclosed biological information measurement device, the identification result information generation unit generates the identification result information when an instruction to end the measurement of the biological information is issued, and the correctness determination unit determines the correctness of the biological information stored in the storage medium after the measurement of the biological information is started until the instruction is issued, based on the identification result information.

In the disclosed biological information measurement device, the identification result information generation unit generates the identification result information at preset time, and the correctness determination unit determines the correctness of the biological information, for which the correctness determination has not been completed, of the biological information stored in the storage medium after the measurement of the biological information is started until the preset time, based on the identification result information.

In the disclosed biological information measurement device, the information input request unit requests the input of the identification information at a random timing.

In the disclosed biological information measurement device, the information input request unit requests the input of the identification information at a timing at which the measured biological information exceeds a threshold value, at a timing based on a signal received from an external apparatus or at a timing at which an amount of change of the measured biological information exceeds a threshold value.

In the disclosed biological information measurement device, the information input request unit requests the input of the identification information at a timing at which environment information around the biological information measurement device changes or at a timing at which motion of the user wearing the biological information measurement device stops.

The disclosed biological information measurement device further includes a sleeping determination unit configured to determine whether the user wearing the biological information measurement device is sleeping, and the information input request unit does not request the input of the identification information while the user is sleeping.

A disclosed method for determining correctness of biological information is a method for determining correctness of biological information stored in a storage medium by a biological information measurement device configured to continuously measure the biological information from a living body with being worn on the living body, and includes an information input request step of requesting an input of identification information by an input unit provided in the biological information measurement device for inputting the identification information necessary for personal identification, at each of a plurality of timings after measurement of the biological information is started by the biological information measurement device, a personal identification step of determining whether a user wearing the biological information measurement device is a pre-registered person in synchronization with each of the plurality of timings, based on the identification information input by the input unit, an identification result information generation step of generating identification result information indicative of a relationship between a first number of times that the request is made in the information input request step and a second number of times that the user is determined to be the pre-registered person in the personal identification step, and a correctness determination step of determining correctness of the biological information stored in the storage medium on the basis of the identification result information.

A disclosed program for determining correctness of biological information is a program for determining correctness of biological information stored in a storage medium by a biological information measurement device configured to continuously measure the biological information from a living body with being worn on the living body, and causes a computer to execute an information input request step of requesting an input of identification information by an input unit provided in the biological information measurement device for inputting the identification information necessary for personal identification, at each of a plurality of timings after measurement of the biological information is started by the biological information measurement device, a personal identification step of determining whether a user wearing the biological information measurement device is a pre-registered person in synchronization with each of the plurality of timings, based on the identification information input by the input unit, an identification result information generation step of generating identification result information indicative of a relationship between a first number of times that the request is made in the information input request step and a second number of times that the user is determined to be the pre-registered person in the personal identification step, and a correctness determination step of determining correctness of the biological information stored in the storage medium on the basis of the identification result information.

According to the present invention, it is possible to provide the biological information measurement device, the method for determining correctness of biological information, and the program for determining correctness of biological information capable of sufficiently storing the biological information to be measured from the authorized user while preventing impersonation of the user.

The present invention is particularly convenient and useful for a portable sphygmomanometer and the like.

Although the present invention has been described with reference to the specific illustrative embodiments, the present invention is not limited to the illustrative embodiments and can be diversely changed without departing from the disclosed technical spirit of the present invention.

What is claimed is:

1. A biological information measurement device configured to continuously measure biological information from a living body with being worn on the living body, the biological information measurement device comprising:
   a storage control unit configured to perform storage control of the measured biological information in a storage medium;
   an input unit for inputting identification information necessary for personal identification;
   an information input request unit configured to request an input of the identification information by the input unit at each of a plurality of timings after measurement of the biological information is started;
   a personal identification unit configured to determine whether a user wearing the biological information measurement device is a pre-registered person in synchronization with each of the plurality of timings, based on the identification information input by the input unit;
   an identification result information generation unit configured to generate identification result information indicative of a relationship between a first number of times that the request is made by the information input request unit and a second number of times that the user is determined to be the pre-registered person by the personal identification unit; and
   a correctness determination unit configured to determine correctness of the biological information stored in the storage medium on the basis of the identification result information.

2. The biological information measurement device according to claim 1, wherein
   the identification result information is a ratio of the second number of times to the first number of times, and
   when the ratio exceeds a threshold value, the correctness determination unit determines that the biological information stored in the storage medium is correct, and when the ratio is equal to or smaller than the threshold value, the correctness determination unit determines that the biological information stored in the storage medium is incorrect.

3. The biological information measurement device according to claim 1, wherein
   the identification result information is a ratio of a third number of times, which is obtained by subtracting the second number of times from the first number of times, to the first number of times, and
   when the ratio is smaller than a threshold value, the correctness determination unit determines that the biological information stored in the storage medium is correct, and when the ratio is equal to or greater than the threshold value, the correctness determination unit determines that the biological information stored in the storage medium is incorrect.

4. The biological information measurement device according to claim 2, wherein
   the threshold value is selected and used from a plurality of values.

5. The biological information measurement device according to claim 3, wherein
   the threshold value is selected and used from a plurality of values.

6. The biological information measurement device according to claim 1, wherein
   the identification result information generation unit generates the identification result information when an instruction to end the measurement of the biological information is issued, and
   the correctness determination unit determines the correctness of the biological information stored in the storage medium after the measurement of the biological information is started until the instruction is issued, based on the identification result information.

7. The biological information measurement device according to claim 1, wherein
   the identification result information generation unit generates the identification result information at preset time, and
   the correctness determination unit determines the correctness of the biological information, for which the correctness determination has not been completed, of the biological information stored in the storage medium after the measurement of the biological information is started until the preset time, based on the identification result information.

8. The biological information measurement device according to claim 1, wherein
the information input request unit requests the input of the identification information at a random timing.

9. The biological information measurement device according to claim 1, wherein
the information input request unit requests the input of the identification information at a timing at which the measured biological information exceeds a threshold value, at a timing based on a signal received from an external apparatus or at a timing at which an amount of change of the measured biological information exceeds a threshold value.

10. The biological information measurement device according to claim 1, wherein
the information input request unit requests the input of the identification information at a timing at which environment information around the biological information measurement device changes or at a timing at which motion of the user wearing the biological information measurement device stops.

11. The biological information measurement device according to claim 1, further comprising a sleeping determination unit configured to determine whether the user wearing the biological information measurement device is sleeping, wherein
the information input request unit does not request the input of the identification information while the user is sleeping.

12. A method for determining correctness of biological information stored in a storage medium by a biological information measurement device configured to continuously measure the biological information from a living body with being worn on the living body, the method comprising:
requesting an input of identification information by an input unit provided in the biological information measurement device for inputting the identification information necessary for personal identification, at each of a plurality of timings after measurement of the biological information is started by the biological information measurement device;
determining whether a user wearing the biological information measurement device is a pre-registered person in synchronization with each of the plurality of timings, based on the identification information input by the input unit;
generating identification result information indicative of a relationship between a first number of times that the request is made and a second number of times that the user is determined to be the pre-registered person; and
determining correctness of the biological information stored in the storage medium on the basis of the identification result information.

13. A non-transitory computer readable medium in which a program causing a computer to execute the method according to claim 12 is recorded.

* * * * *